United States Patent [19]

Ducatman et al.

[11] Patent Number: 4,686,212

[45] Date of Patent: Aug. 11, 1987

[54] STABLE SODIUM ASPIRIN TABLET COMPOSITIONS

[75] Inventors: Fred P. Ducatman, Westfield; John D. Flanagan, Palisades Park, both of N.J.

[73] Assignee: PharmaControl Corp., Englewood Cliffs, N.J.

[21] Appl. No.: 765,086

[22] Filed: Aug. 13, 1985

[51] Int. Cl.⁴ ............................................. A61K 31/62
[52] U.S. Cl. .................................................... 514/161
[58] Field of Search ......................................... 514/161

[56] References Cited

U.S. PATENT DOCUMENTS 3,985,792 10/1976 Galat .................................... 260/480
4,282,215 8/1981 Dudzenski et al. ................. 514/161

Primary Examiner—Stanley J. Friedman
Attorney, Agent, or Firm—Pennie & Edmonds

[57] ABSTRACT

Compositions are provided for the preparation of stable sodium aspirin tablets. The compositions comprise dry, crystalline sodium aspirin, an anhydrous binder that is unreactive to sodium aspirin and a hydrogenated animal or vegetable oil lubricant but lack the traditional tablet disintegrant. Tablets produced from these compositions can be stored for prolonged periods of time yet disintegrate in water at a rate comparable to that of ordinary aspirin.

9 Claims, No Drawings

STABLE SODIUM ASPIRIN TABLET COMPOSITIONS

TABLE OF CONTENTS

Technical Field
Background of the Invention
Summary of the Invention
Detailed Description of the Invention
Examples
  Instability of Sodium Aspirin in Traditional Tablet Compositions
  Stability of Sodium Aspirin in the Compositions of the Invention
  Disintegration of Tablets Prepared from Compositions Lacking a Disintegrant

TECHNICAL FIELD

The present invention relates to superior analgesic, anti-arthritic, anti-inflammatory and anti-pyretic tablet compositions which contain sodium aspirin but lack the disintegrants that are typically employed in tablet manufacture. Despite a strong tendency for sodium aspirin to absorb moisture and to decompose, the compositions of the invention are stable to prolonged storage. This stability to storage is due to the nature of the ingredients of the compositions and to effective packaging methods.

BACKGROUND OF THE INVENTION

The most widely used analgesic and anti-inflammatory drug is aspirin, which remains the drug of choice for the treatment of arthritis and common aches and pains. Unfortunately, the use of aspirin, the chemical name of which is acetylsalicylic acid, can be accompanied by undesirable side effects. These side effects include gastric mucosal irritation, gastric distress and intolerance and are due to the acidic character of aspirin and to its poor water solubility. Once ingested, aspirin tablets disintegrate, leaving insoluble particles which lodge in and irritate the gastric mucosa. Because of the irritation caused by conventional aspirin, many individuals taking aspirin suffer gastric distress. Acetaminophen (as present in Tylenol, Datril etc.) is sometimes taken instead of aspirin to avoid gastric distress, but this compound is ineffective in reducing inflammation. Arthritic patients who suffer from inflammation but cannot tolerate aspirin must thus turn to other, more dangerous drugs.

In efforts to overcome the shortcomings of ordinary aspirin, a number of approaches have been explored. There are available today a number of buffered aspirin compositions such as Bufferin, Excedrin and Anacin. These compositions neutralize some gastric acid but do not eliminate the basic problem—insoluble aspirin particles form which persist in causing gastric mucosal irritation.

Aspirin could be formulated into enteric coated tablets, but such formulations would merely shift the locus of irritation to the duodenal mucosa and to other regions of the gastrointestinal tract, where the tablets would disintegrate.

More effective are compositions similar to Alka-Seltzer, which produce a soluble form of aspirin upon contact with water that is readily assimilated by the body and which, therefore, does not cause localized irritation. But the way such compositions accomplish this objective is not very efficient. Large quantities of sodium bicarbonate are employed which may exceed the weight of the aspirin contained by a factor of ten or more. The preparations are also costly for the analgesic dose they provide, and they can produce distending quantities of gas. As a result, they are practically never used by arthritic patients or by individuals with chronic pain or inflammation.

The sodium salt derivative of aspirin produced when Alka-Seltzer dissolves in water would prove beneficial if it could be isolated free of excess bicarbonate salt and formulated into a convenient dosage form, but severe problems of stability make the attainment of both of these objectives difficult. The preparation of sodium aspirin in aqueous solution, is an easy task, but removal of the water to yield useable solid crystals is difficult. The acetate group of sodium aspirin tends to hydrolyze to produce salicylic acid during the dehydration of the compound. Granular plate-like crystals of sodium aspirin have been produced by Galat (U.S. Pat. No. 3,985,792) in a process involving precipitation of the compound from aqueous solution and removal of the water of hydration. But, formulation of the pure, anhydrous compound into a useable dosage form presents further, severe stability problems.

The typical tablet formulation consists of an active ingredient, a bulking agent, a binder, a lubricant and a disintegrant. The latter ingredient is generally needed to ensure rapid decomposition of the tablet and hence ready availability of the active ingredient. Unfortunately, when sodium aspirin is the active ingredient in such a composition, it undergoes unacceptably rapid degradation to salicylic acid.

SUMMARY OF THE INVENTION

Compositions are provided that are useful for the preparation of stable sodium aspirin tablets. Sodium aspirin offers marked therapeutic advantages over conventional aspirin or aspirin combined with a buffering compound because its ready solubility assures rapid uptake by the body and precludes local irritation of the gastrointestinal mucosa. Sodium aspirin is also highly hygroscopic, however, and upon contact with moisture, the compound decomposes to salicylic acid and sodium acetate.

The compositions of the invention avoid this decomposition by providing tablet binders and lubricants that are anhydrous and otherwise unreactive to sodium aspirin and by eliminating the disintegrants that are normally employed in tablet making compositions. Dry, crystalline sodium aspirin is used in conjunction with these binders and lubricants.

The compositions of the invention comprise on a weight basis from about 40 to about 90%, preferably from about 70 to about 85%, of dry, crystalline sodium aspirin; from about 0.1 to about 10%, preferably from about 0.5 to about 5%, of a hydrogenated animal or vegetable oil lubricant; and from about 5 to about 25% of an anhydrous binder that is unreactive to sodium aspirin. The hydrogenated animal or vegetable oil lubricant should be substantially free of free fatty acids, because such fatty acids are reactive to the sodium aspirin. The binder preferably consists of polyethylene glycol or microcrystalline wax, both of which are combined with about an equal weight of dibasic calcium phosphate or anhydrous lactose.

Tablets produced using the compositions of the invention may be swallowed directly with water or a beverage, or they may first be dissolved in such fluids. Despite the lack of a disintegrant, the compositions of the invention rapidly dissolve in water or beverages at a rate comparable to that of ordinary aspirin, but without imparting an undesirable taste. The analgesic and other effects of the compositions are thus readily available to children or to older individuals who cannot or will not swallow tablets. The disintegration rate of the tablets in water is comparable to that of ordinary aspirin, despite the lack of a disintegrant.

DETAILED DESCRIPTION OF THE INVENTION

The present invention relates to novel analgesic, anti-arthritic, anti-inflammatory and anti-pyretic compositions containing dry, crystalline sodium aspirin and lubricants and binders which can be formulated into convenient tablet dosage forms that are stable to long term storage. Investigations showed that when sodium aspirin is combined with disintegrants such as corn starch or derivatives thereof, potato starch, sodium starch glycollate, alginic acid, microcrystalline cellulose or PVP XL (a commercial cross-linked Povidone) which are traditionally used in tablet compositions, the sodium aspirin undergoes substantial decomposition to salicyclic acid and sodium acetate over a storage period of only one month (see Section 5.1, below). Ordinarily, such disintegrants must be present in a tablet to ensure that the tablet will disintegrate in a reasonable time. Unexpectedly, it has been found that sodium aspirin may be formulated into a tablet composition which lacks a disintegrant and is thus stable but which nevertheless rapidly disintegrates in water or in a variety of beverages such as milk or fruit juices.

Any dry, crystalline sodium aspirin may be used as long as its granular consistency is such that it can readily be manipulated and pelleted in conventional tableting machinery. Sodium aspirin having a plate-like crystalline structue can be prepared by the method of Galat (U.S. Pat. No. 3,985,792, hereby incorporated by reference). The sodium aspirin of the present invention is preferably prepared by the method of Galat. On a weight basis, the sodium aspirin content of the compositions of the invention may range from about 40 to about 90%, with a range of from about 70 to about 85% preferred. As the percentage of sodium aspirin decreases below 40%, the size of a tablet needed for an effective dose becomes impractically large.

The binders of the invention must be anhydrous and otherwise unreactive to sodium aspirin and should possess a woking consistency that is suitable for use in tableting equipment. Binders meeting these requirements are polyethylene glycol or microcrystalline wax, both of which are combined with an approximately equal weight of either dibasic calcium phosphate or anhydrous lactose. The dibasic calcium phosphate and anhydrous lactose make the compositions compressible and impart cohesiveness to them. The particle size ranges of these ingredients are from about 74 microns (200 mesh) to about 840 microns (20 mesh).

Polyethylene glycol (PEG), also known as macrogol, Carbowax, Jeffox, Nycoline, Pluracol E, Poly-G, Polyglycol E or Solbase, is an α-hydro-ω-hydroxypoly(oxy-1,2-ethanediyl) polymer having the general formula $H(OCH_2CH_2)_nOH$, where n is an integer greater than or equal to 4. Although PEG is available as PEG 1000, 1450, 3350, 8000, 20000 and in other sizes (the numbers indicate the mean molecular weight of the material), PEG 8000 is preferred. The lower weight materials are too soft for easy manipulation at room temperature, while the flakes of the higher weight material are too coarse. The particle size range of the preferred PEG 8000, (a product of Union Carbide, Danbury, Conn.) is about 50 microns (275 mesh) to about 1200 microns (16 mesh).

Microcrystalline wax, which is useable but not as effective as PEG, is a finely milled waxy material that is a mixture of straight chain, branched chain and cyclic hydrocarbons, obtained by solvent fractionation of the still bottom fraction of petroleum by suitable dewaxing or deoiling methods. Microcrystalline was produced by Ross Laboratories, Jersey City, N.J., has a particle size distribution ranging from about 74 microns (200 mesh) to about 840 microns (20 mesh).

The binder content of the compositions of the invention may range on a weight basis from about 5 to about 25%.

The lubricants of the compositions of the invention are hydrogenated vegetable oils. These oils are preferably refined and bleached, and they may consist of mixtures of the triglycerides of stearic and palmitic acid or other similar acids. In a preferred embodiment, a lubricant called "Sterotex" is used. Sterotex is the trademark for a hydrogenated vegetable oil product of Capitol City Products, Columbus, Ohio which is produced in a particle size range of from about 40 microns (325 mesh) to about 250 microns (60 mesh).

The amount of lubricant may range from about 0.1 to about 10 weight percent, but a range of from about 0.5 to about 5% is preferred.

In one preferred embodiment, designated Formula 52, the composition comprises on a weight basis about 80% dry, crystalline sodium aspirin, 10% PEG 8,000, 8.5% dibasic calcium phosphate and 1.5% Sterotex. In another preferred embodiment, called Formula 53, the composition comprises on a weight basis about 80% dry, crystalline sodium aspirin, 9% PEG 8000, 8.5% anhydrous lactose and 2.5% Sterotex. Tablets having dimensions of 12.42×7.81 mm made with either of these compositions disintegrate rapidly in water yet display remarkable stability upon storage. Both tablets undergo about 3% or less decomposition after storage for up to three months at 40° C., as judged by analysis for free salicylic acid.

To ensure stability, the composition of the invention should be prepared in a facility having no more than 30%, and preferably less than 20%, relative humidity. Standard dehumidifying equipment can be used to maintan a suitable environment. During storage, the tablets prepared with the compositions of the invention are best sealed in individual foil or plastic packages, or kept in tightly capped glass or plastic containers, which in turn should be kept in a moisture proof pouch.

Tablets prepared with the compositions of the invention may be made to contain any suitable sodium aspirin dose such as the 5 grain dose that is standard for conventional aspirin. The tablets may be swallowed along with water or a beverage, or they may first be dissolved in water, milk, fruit juice etc., for individuals who cannot or will not swallow tablets.

EXAMPLES

The present invention may be more readily understood by reference to the following, non-limiting examples.

INSTABILITY OF SODIUM ASPIRIN IN TRADITIONAL TABLET COMPOSITIONS

To demonstrate the problem of maintaining sodium aspirin free from substantial degradation, the compound was incorporated into traditional tablet compositions contaning a disintegrant, and tablets produced therefrom were allowed to stand at various temperatures in tightly stoppered glass containers. After one or two months, the tablets were analyzed for the presence of salicylic acid by high performance liquid chromatography (HPLC) in a Burdick & Jackson OD5, C-18, 5 micron 150×4.6 mm column in acetonitrile: water: formic acid (35:65:0.2) at a flow rate of 1.5 ml/minute. The column effluent was monitored spectrophotometrically at 280 mm, and the area under the peaks shown by standards to be salicylic acid was integrated with a Data Module No. 730 electronic integrator (Waters Associates, Milford, Mass.) to establish the degree of decomposition. The results, representing the average values for 10 samples under each storage condition are shown in Table 1.

TABLE 1

DEGRADATION OF SODIUM ASPIRIN IN TABLETS CONTAINING A DISINTEGRANT

| Formula No. | Components | Storage Conditions | Salicylic Acid (%) |
|---|---|---|---|
| 1 | 82.3% Sodium Aspirin | 1 month/40° C. | 8.2 |
|   | 8% PVP XL[a] | 1 month/37° C. | 8.1 |
|   | 7% Avicel ph101[b] | 2 months/25° C. | 6.6 |
|   | 1.5% Stearic Acid |  |  |
|   | 1% Syloid 72[c] |  |  |
| 2 | 80% Sodium Aspirin | 1 month/40° C. | 19.9 |
|   | 19.7% Avicel ph101[b] | 1 month/37° C. | 27.4 |
|   | 0.3% Magnesium Stearate |  |  |
| 3 | 49.86% Sodium Aspirin | 1 month/40° C. | 7.1 |
|   | 49.86% Micro-Crystalline Cellulose | 1 month/37° C. | 6.2 |
|   | 0.28% Magnesium Stearate |  |  |

[a]PVP XL is a cross-linked Povidone disintegrant produced by GAF Corporation, Wayne, New Jersey.
[b]Avicel ph101 is a fine particle crystalline cellulose disintegrant made by FMC Corporation, Philadelphia, Pennsylvania.
[c]Syloid 72 is a silicone dioxide glidant produced by W. R. Grace & Company, New York, New York.
[d]Microcrystalline cellulose is a disintegrant product of Wei Ming Pharmaceutical Co., Ltd., which was obtained from ICD Group, Inc., New York, New York.

In formula 1 of Table 1, the PVP XL and Avicel ph101 together acted as a binder-disintegrant. Stearic acid was used as a lubricant, and Syloid 72 was a glidant or flow aid. In formula 2 of the table, Avicel ph101 alone was the binder-disintegrant, and magnesium stearate the lubricant. In formula 3, microcrystalline cellulose acted as a binder-disintegrant, and magnesium stearate was the lubricant.

As shown in Table 1, for the disintegrant-containing formulas the breakdown of sodium aspirin to salicylic acid ranged from 6.2 to 27.4% over a period of 2 months or less. This degree of decomposition makes such compositions unuseable, because the United States Pharmacopeia (USP) specification for buffered aspirin tablets allows free salicylic acid levels only up to 3.0% (USP XXI, p. 78). Starch was also evaluated as a disintegrant, but after only one week at 40° C., 30% of the sodium aspirin had broken down to salicylic acid.

STABILITY OF SODIUM ASPIRIN IN THE COMPOSITIONS OF THE INVENTION

In marked coontrast to the results shown above, with the compositions of the present invention sodium aspirin degradation is minimal. To illustrate this fact, sodium aspirin tablets produced from preferred compositions formulas No. 52 and 53 (described above in Section 4) were incubated in sealed glass containers or foil pouches and analyzed for salicylic acid by HPLC as described above, with the results shown in Table 2. These results represent the average values for 10 samples under each storage condition.

TABLE 2

STABILITY OF SODIUM ASPIRIN IN THE ABSENCE OF A DISINTEGRANT

| Formula No.[a] | Storage Conditions | Salicylic Acid (%) |
|---|---|---|
| 52 | Bottles at 40° C. for 1 month | 1.4 |
|    | Bottles at 40° C. for 2 months | 1.7 |
|    | Bottles at 40° C. for 3 months | 2.5 |
|    | Foil pouches at 40° C. for 1 month | 1.1 |
|    | Foil pouches at 40° C. for 2 months | 1.6 |
|    | Foil pouches at 37° C. for 2 months | 1.3 |
| 53 | Bottles at 40° C. for 1 month | 2.0 |
|    | Bottles at 40° C. for 2 months | 2.3 |
|    | Bottles at 40° C. for 3 months | 3.3 |
|    | Foil pouches at 40° C. for 1 month | 1.7 |
|    | Foil pouches at 40° C. for 2 months | 2.4 |
|    | Foil pouches at 37° C. for 2 months | 2.2 |

[a]The compositions of formulas No. 52 and 53 were as described above in Section 4.

As shown in Table 2, the stability of the sodium aspirin in formula No. 52 was somewhat better than that of the compound in formula No. 53. Nevertheless, in both formulas the stability of the sodium aspirin after 3 months storage was far better than that observed for any of the compositions containing a disintegrant (Table 1) after only one month.

DISINTEGRATION OF TABLETS PREPARED FROM COMPOSITIONS LACKING A DISINTEGRANT

As noted above, the compositions of the invention can be used to produce tablets that undergo little decomposition, even after 3 months storage at an elevated temperature of 40° C. To show that such tablets lacking a disintegrant nevertheless disintegrate rapidly in water, their rate of disintegration in water was measured using the USP disintegration test (USP XXI, p. 1242).

Briefly, a partitioned basket assembly having 6 open-ended chambers, each of which contained a tablet to be tested, was mechanically raised and lowered in a 1-liter beaker containing 37° C. water at a frequency of 40 cycles per minute through a distance of between 5 and 6 cm. The basket assembly was made by Erweka, Inc., Fairfield, Conn., and so constructed that fragments from the disintegrating tablets traversed a wire mesh at the bottom of the basket. Complete disintegration of the tablets was denoted by the occurrence of a positive electrical signal, the time of occurrence of which was carefully noted.

The disintegration tests showed that 12.42×7.81 mm tablets produced from the compositions of the present invention all disintegrated completely in 3.5 minutes despite the absence of a disintegrant. This disintegration time compares quite favorably with that of ordinary aspirin containing a disintegrant. The USP standard for the disintegration of aspirin tablets is 5 minutes (USP reference).

Many modifications and variations of the present invention may be made without departing from its spirit and scope, as will become apparent to those skilled in the art. The specific embodiments described herein are offered by way of example only, and the invention is limited only by the terms of the appended claims.

What is claimed is:

1. A stable sodium aspirin tablet composition consisting essentially of about 40 to about 90% dry, crystalline sodium aspirin and a plurality of tableting adjuvants, each of the tableting adjuvants being substantially anhydrous and essentially unreactive to sodium aspirin, the tableting adjuvants consisting essentially of from about 5 to about 25% of a substantially anhydrous binder and from about 0.1 to about 10% of hydrogenated animal or vegetable oil lubricant which is substantially free of fatty acids.

2. The composition of claim 1 wherein on a weight basis the sodium aspirin is present at from about 40 to about 90%, the binder is present at from about 5 to about 25%, and the lubricant is present at from about 0.1 to about 10%.

3. The stable sodium aspirin tablet composition of claim 1 wherein on a weight basis the sodium aspirin is present from about 70 to about 85%, the binder is present from about 5 to about 25%, and the lubricant is present at from about 0.5 to about 5%.

4. The stable sodium aspirin tablet composition of claim 1 wherein the binder is a mixture of polyethylene glycol and about an equal weight of dibasic calcium phosphate or anhydrous lactose.

5. The stable sodium aspirin tablet composition of claim 3 wherein the binder is a mixture of polyethylene glycol and about an equal weight of dibasic calcium phosphate or anhydrous lactose.

6. The stable sodium aspirin tablet composition of claim 1 wherein the binder is a mixture of microcrystalline wax and about an equal weight of dibasic calcium phosphate or anhydrous lactose.

7. The stable sodium aspirin tablet composition of claim 3 wherein the binder is a mixture of microcrystalline wax and about an equal weight of dibasic calcium phosphate or anhydrous lactose.

8. A stable sodium aspirin tablet composition comprising on a weight basis about 80% dry, crystalline sodium aspirin, about 10% PEG 8000, about 8.5% dibasic calcium phosphate and about 1.5% Sterotex.

9. A stable sodium aspirin tablet composition comprising on a weight basis about 80% dry, crystalline sodium aspirin, about 9% PEG 8000, about 8.5% anhydrous lactose and about 2.5% Sterotex.

* * * * *